US00RE50585E

(19) United States
(12) Reissued Patent
Jacobs et al.

(10) Patent Number: US RE50,585 E
(45) Date of Reissued Patent: Sep. 16, 2025

(54) CLOSURE DEVICE FOR SEALING PERCUTANEOUS OPENING IN A VESSEL

(71) Applicant: Teleflex Life Sciences LLC, Wilmington, DE (US)

(72) Inventors: Peter Jacobs, St. Louis Park, MN (US); Thomas Holman, Princeton, MN (US); Chad Kugler, Buffalo, MN (US)

(73) Assignee: Teleflex Life Sciences LLC, Wilmington, DE (US)

(21) Appl. No.: 17/873,859

(22) Filed: Jul. 26, 2022

Related U.S. Patent Documents

Reissue of:
(64) Patent No.: 10,722,225
Issued: Jul. 28, 2020
Appl. No.: 15/920,665
Filed: Mar. 14, 2018

U.S. Applications:
(62) Division of application No. 15/040,023, filed on Feb. 10, 2016, now Pat. No. 10,016,188.
(Continued)

(51) Int. Cl.
*A61B 17/00* (2006.01)

(52) U.S. Cl.
CPC ..... *A61B 17/0057* (2013.01); *A61B 2017/00619* (2013.01); *A61B 2017/00623* (2013.01)

(58) Field of Classification Search
CPC ..... A61B 17/0057; A61B 2017/00597; A61B 2017/00606; A61B 2017/00615;
(Continued)

(56) References Cited

U.S. PATENT DOCUMENTS 5,108,420 A 4/1992 Marks
5,222,974 A 6/1993 Kensey et al.
(Continued)

FOREIGN PATENT DOCUMENTS

CA 2238784 C 8/2003
EP 2497426 A1 9/2012
(Continued)

OTHER PUBLICATIONS

Partial Search Report and Invitation to Pay Additional Fees mailed Jul. 7, 2016, in connection with PCT Application No. PCT/US2016/017238.

(Continued)

*Primary Examiner* — Matthew J Kasztejna
(74) *Attorney, Agent, or Firm* — Dorsey & Whitney LLP

(57) ABSTRACT

Closure systems, kits and methods for sealing a percutaneous puncture or other opening in a blood vessel wall, body cavity or biopsy tract are disclosed. A closure system can comprise an implant assembly, a delivery assembly, and an introducer sheath. The closure system can further comprise a valve bypass and a dilator. The implant assembly can include an inner member, a sealing membrane, and an outer member, each of which can be delivered by the delivery assembly. The inner member can be extended through the puncture or opening and positioned adjacent an inner tissue surface. The outer member can be positioned adjacent an outer tissue surface. The sealing membrane can have a distal end attached to the inner member, a proximal end including an opening configured to receive the outer member, and a mid-region therebetween. The outer member, when expanded from a delivery configuration to a sealing configuration, can urge the mid-region of the sealing membrane radially outward such that its outer surface can contact and conform to a perimeter edge of the puncture or opening.

10 Claims, 10 Drawing Sheets

Related U.S. Application Data

(60) Provisional application No. 62/114,101, filed on Feb. 10, 2015.

(58) Field of Classification Search
CPC ..... A61B 2017/00628; A61B 2017/00623; A61B 2017/00004
See application file for complete search history.

(56) References Cited

U.S. PATENT DOCUMENTS 5,282,827 A 2/1994 Kensey et al.
5,350,399 A 9/1994 Erlebacher et al.
RE34,866 E 2/1995 Kensey et al.
5,411,520 A 5/1995 Nash et al.
5,486,195 A 1/1996 Myers et al.
5,531,759 A 7/1996 Kensey et al.
5,556,376 A 9/1996 Yoon
5,620,461 A 4/1997 Moer et al.
5,662,681 A 9/1997 Nash et al.
5,676,689 A 10/1997 Kensey et al.
5,700,277 A 12/1997 Nash et al.
5,782,860 A 7/1998 Epstein et al.
5,853,422 A 12/1998 Huebsch et al.
5,861,003 A 1/1999 Latson et al.
5,925,060 A 7/1999 Forber
5,976,174 A 11/1999 Ruiz
6,024,756 A 2/2000 Huebsch et al.
6,071,300 A 6/2000 Brenneman et al.
6,080,182 A 6/2000 Shaw et al.
6,183,496 B1 2/2001 Urbanski
6,190,400 B1 2/2001 Moer et al.
6,328,757 B1 12/2001 Matheny
6,331,184 B1 12/2001 Abrams
6,425,911 B1 7/2002 Akerfeldt et al.
6,508,828 B1 1/2003 Akerfeldt et al.
6,860,895 B1 3/2005 Akerfeldt et al.
7,144,410 B2 12/2006 Marino et al.
7,621,937 B2 11/2009 Pipenhagen et al.
7,658,748 B2 2/2010 Marino et al.
7,875,052 B2 1/2011 Kawaura et al.
7,931,671 B2 4/2011 Tenerz
8,029,522 B2 10/2011 Ortiz et al.
8,057,510 B2 11/2011 Ginn et al.
8,070,772 B2 12/2011 McGuckin et al.
8,083,768 B2 12/2011 Ginn et al.
8,105,352 B2 1/2012 Egnelöv
8,192,456 B2 6/2012 Holman et al.
8,192,457 B2 6/2012 Coleman et al.
8,252,022 B2 8/2012 Holman et al.
8,267,959 B2 9/2012 Fällman
8,323,305 B2 12/2012 Epstein et al.
8,366,742 B2 2/2013 Coleman et al.
8,382,795 B2 2/2013 Forsberg et al.
8,398,676 B2 * 3/2013 Roorda ..... A61B 17/0057 606/213
8,480,706 B2 7/2013 Chanduszko et al.
8,500,776 B2 8/2013 Ebner
8,597,324 B2 12/2013 Briganti et al.
8,685,059 B2 4/2014 Walters
8,747,435 B2 6/2014 Yassinzadeh
8,870,914 B2 10/2014 Hoffman et al.
8,906,050 B2 12/2014 Brett et al.
9,060,751 B2 6/2015 Martin et al.
9,655,603 B2 5/2017 Tegels et al.
9,770,233 B2 9/2017 Nelson
10,722,225 B2 7/2020 Jacobs et al.
2002/0099448 A1 7/2002 Hiles et al.
2002/0173820 A1 11/2002 Akerfeldt et al.
2002/0198562 A1 12/2002 Akerfeldt et al.
2003/0023267 A1 1/2003 Ginn
2003/0050665 A1 3/2003 Ginn
2004/0093025 A1 5/2004 Egnelov
2006/0009800 A1 1/2006 Christianson et al.
2006/0173492 A1 8/2006 Akerfeldt et al.
2006/0241579 A1 10/2006 Kawaura et al.
2006/0265008 A1 11/2006 Maruyama et al.
2007/0031508 A1 2/2007 Armstrong et al.
2007/0083232 A1 4/2007 Lee
2007/0135842 A1 6/2007 Moer et al.
2007/0225757 A1 9/2007 Preinitz et al.
2008/0091235 A1 * 4/2008 Sirota ..... A61B 17/0057 606/215
2008/0097509 A1 4/2008 Beyar et al.
2008/0147038 A1 6/2008 Hoffman
2008/0249562 A1 10/2008 Cahill
2009/0143815 A1 6/2009 Eidenschink et al.
2009/0171281 A1 7/2009 Pipenhagen et al.
2009/0216267 A1 8/2009 Willard et al.
2009/0234377 A1 9/2009 Mahlin et al.
2009/0270885 A1 10/2009 Maruyama et al.
2010/0087854 A1 * 4/2010 Stopek ..... C07D 471/04 606/215
2010/0100107 A1 4/2010 Duggal et al.
2010/0217308 A1 8/2010 Hansen
2010/0217311 A1 8/2010 Jenson et al.
2010/0256673 A1 * 10/2010 Coleman ..... A61B 17/0057 606/215
2010/0275432 A1 11/2010 Pikus et al.
2011/0029012 A1 2/2011 Tegels
2011/0066181 A1 3/2011 Jenson et al.
2011/0196388 A1 8/2011 Thielen et al.
2012/0022562 A1 1/2012 Willard
2012/0065667 A1 3/2012 Javois et al.
2012/0089177 A1 4/2012 Tegels
2012/0116447 A1 5/2012 Stanley et al.
2012/0143245 A1 6/2012 Tegels
2012/0158004 A1 6/2012 Burger et al.
2012/0158044 A1 * 6/2012 Jenson ..... A61B 17/0057 606/213
2012/0209323 A1 8/2012 Uchida et al.
2012/0245625 A1 9/2012 Coleman et al.
2013/0006297 A1 1/2013 Drasler
2013/0041395 A1 2/2013 Canniere
2013/0138149 A1 5/2013 Tegels
2013/0190810 A1 7/2013 Roorda et al.
2013/0274795 A1 10/2013 Grant et al.
2014/0018846 A1 1/2014 Grant et al.
2014/0052171 A1 * 2/2014 Tegels ..... A61B 17/0057 606/213
2014/0114346 A1 4/2014 McCaffrey
2014/0114347 A1 * 4/2014 Stanley ..... A61B 17/0057 606/213
2014/0142620 A1 5/2014 Marchi et al.
2014/0163608 A1 6/2014 Osypka
2014/0172012 A1 6/2014 Stanley et al.
2014/0194925 A1 7/2014 Lim et al.
2014/0207183 A1 7/2014 Shipp
2014/0207184 A1 7/2014 Shipp
2014/0222064 A1 * 8/2014 Tegels ..... A61B 17/0057 606/213
2014/0236222 A1 8/2014 Tegels
2014/0236224 A1 8/2014 Tegels
2014/0236225 A1 8/2014 Tegels et al.
2014/0249575 A1 9/2014 Mylonakis et al.
2014/0257375 A1 9/2014 Tegels
2014/0277113 A1 9/2014 Stanley et al.
2014/0336672 A1 * 11/2014 Walters ..... A61B 17/0057 606/139
2014/0345109 A1 11/2014 Grant et al.
2015/0051641 A1 2/2015 Baxter
2015/0057705 A1 2/2015 Vidlund
2016/0038129 A1 * 2/2016 Shipp ..... A61B 17/0057 606/213
2016/0199049 A1 7/2016 Sluis
2016/0256141 A1 9/2016 Mendez et al.
2016/0374655 A1 12/2016 Walters et al.
2017/0189001 A1 7/2017 Stanley et al.
2017/0215853 A1 8/2017 Stanley et al.

FOREIGN PATENT DOCUMENTS

EP 2258258 A3 4/2013
JP 2007252917 A 10/2007

(56) References Cited

FOREIGN PATENT DOCUMENTS

| | | | |
|---|---|---|---|
| WO | 2007149989 | A3 | 9/2008 |
| WO | 2014141209 | A1 | 9/2014 |
| WO | 2015165117 | A1 | 11/2015 |

OTHER PUBLICATIONS

Extended European Search Report and Search Opinion mailed Jan. 12, 2023 in EP Patent Application No. 22205655.8.
Examination Report pursuant to Article 94(3) issued in Europe for EP Patent Application No. 22205655.8, dated May 21, 2025, 8 pgs.
Partial Search Report and Invitation to Pay Additional Fees dated Jul. 7, 2016, in connection with PCT Application No. PCT/US2016/017238.

* cited by examiner

CLOSURE DEVICE FOR SEALING PERCUTANEOUS OPENING IN A VESSEL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CLAIM OF PRIORITY

This *is an application for reissue of U.S. Pat. No. 10,722,225, entitled "Closure Device for Sealing Percutaneous Opening In a Vessel" and filed on Mar. 14, 2018, which* is a divisional application of U.S. Non-Provisional patent application Ser. No. 15/040,023, now U.S. Pat. No. 10,016,188, entitled "CLOSURE DEVICE FOR SEALING PERCUTANEOUS OPENING IN A VESSEL" and filed on Feb. 10, 2016, which claims the benefit of priority under 35 U.S.C. § 119(e) to U.S. Provisional Patent Application Ser. No. 62/114,101, entitled "IMPLANT ASSEMBLY FOR SEALING PERCUTANEOUS OPENING IN A VESSEL" and filed on Feb. 10, 2015, [both] *the entire disclosures* of *each of* which are herein incorporated by reference in their entireties.

TECHNICAL FIELD

This patent document relates to medical devices. More particularly, but not by way of limitation, the patent document relates to closure systems, kits and methods.

BACKGROUND

Catheterization and interventional procedures, such as angioplasty and stenting, are generally performed by inserting a hollow needle through a patient's skin and any intervening tissue into a blood vessel of the vascular system. A guidewire can then be passed through a lumen of the needle into the blood vessel accessed by the needle. The needle can be removed, and an introducer sheath in conjunction with, or subsequent to, a dilator can be advanced over the guidewire and into the vessel. The introducer sheath can facilitate introducing various devices into the vessel, while minimizing trauma to the vessel wall or minimizing blood loss during a procedure. For example, a catheter can be advanced through a lumen of the introducer sheath and over the guidewire into a position for performing an interventional procedure.

Upon completion of the interventional procedure, for example, the catheter and introducer sheath can be removed, leaving a puncture in the vessel wall. The puncture tends to bleed, particularly in the case of arterial punctures because of the higher arterial blood pressure as compared to venous blood pressure. Until the puncture is closed, clinical complications can result leading to increased hospital stays and costs. To address this concern, medical personnel are required to provide constant and continuing care to patients who have undergone an interventional procedure involving an arterial or venous puncture to ensure that post-operative bleeding is controlled.

A common method of controlling a puncture in a vessel wall is to maintain external pressure (e.g., human hand pressure) over the vessel until the puncture seals by natural clot formation processes. This method of puncture closure typically takes between 30 and 90 minutes, with the length of time being greater if the patient is hypertensive or anti-coagulated. Utilizing external pressure to control bleeding can suffer from several drawbacks regardless of whether the patient is hypertensive or anti-coagulated. For example, human hand pressure can be uncomfortable for the patient, can result in excessive restriction or interruption of blood flow, and can consume costly time and effort on the part of the hospital staff. Other pressure techniques, such as pressure bandages, sandbags and clamps can also suffer from drawbacks, including requiring the patient to remain motionless for an extended period of time and requiring close monitoring of the patient by hospital staff to ensure effectiveness of these techniques.

Overview

The present inventors recognize that an ever-expanding range of catheterization and interventional procedures and a changing reimbursement landscape, with an increasing adoption of outpatient interventions, drive the need for more efficient puncture closure at the end of procedures. The present inventors further recognize that with an ever-increasing number of procedures requiring large introducer sheaths, such as abdominal aortic aneurysm repair, thoracic aneurysm repair, transcutaneous aortic valve implantation (TAVI), trans-septal occluder implantation and implantation of a variety of percutaneous ventricular-assist devices, the ability to achieve closure following sheath removal is increasingly important. According to existing techniques, when large introducer sheaths are used during a percutaneous procedure, a surgical cut-down is often performed to expose the femoral artery and a labor-intensive suture procedure is used to establish vessel wall closure.

The present closure systems, kits and methods can be used to seal a percutaneous puncture or other opening in a blood vessel wall, body cavity or biopsy tract. The present teachings have particular relevance to reliably and consistently sealing a puncture access site opening in a vessel following a TAVI procedure or delivery or use of another large profile interventional device. The teachings can eliminate the prolonged bleeding associated with such punctures, prevent disposing any occlusive material into the vessel, prevent introducing infectious organisms into a patient's circulatory system, and avoid labor-intensive external pressure procedures on the part of hospital staff.

A closure system can comprise an implant assembly, a delivery assembly and an introducer sheath. The closure system can further comprise a valve bypass and a dilator. The implant assembly can include an inner member, a sealing membrane, and an outer member, each of which can be delivered by the delivery assembly. The inner member can be extended through the puncture or opening and positioned adjacent an inner tissue surface. The outer member can be positioned adjacent an outer tissue surface. The sealing membrane can have a distal end attached to the inner member, a proximal end including an opening configured to receive the outer member, and a mid-region therebetween. The outer member, when expanded from a delivery configuration to a sealing configuration, can urge the mid-region of the sealing membrane radially outward such that its outer surface can contact and conform to an edge of the puncture or opening.

The delivery assembly for delivery and deploying the implant assembly can comprise a handle, a rail, a shear tube, a delivery tube, and an actuation member. The handle can have a first housing portion and a second housing portion.

The rail can extend from a first end engaged with the inner member to a second end statically coupled with the second housing portion. The outer member can be supported by the rail between its first and second ends. The shear tube can extend from a first end, which includes a keyed passageway, to a second end engaged with the second housing portion. The delivery tube can concentrically surround portions of the shear tube, be coupled to an end of the sealing membrane on its first end, and be coupled to the first housing portion on its second end. The actuation member can be engaged with the second end of the shear tube to urge the tube in a direction to expand the outer member from its delivery configuration to its sealing configuration.

A method for sealing a puncture that extends between an inner vessel surface and an outer vessel surface can comprise inserting an inner member through the puncture and into a lumen of the vessel. The inner member can be pulled against the inner vessel surface and portions of a connecting member and a sealing membrane, which are coupled on their first ends to the inner member, can be arranged to extend to the outside of the vessel on their second ends. An outer member in a delivery configuration can then be inserted through the second end of the sealing membrane such that the sealing membrane at least partially surrounds the outer member. A compressive force can be applied to the outer member in a distal direction to expand the delivery configuration to a sealing configuration. This expansion can urge a mid-region of the sealing membrane radially outward such that its outer surface contacts and conforms to an edge of the hole.

These and other examples and features of the present systems, kits and methods will be set forth, at least in part, in the following Detailed Description. This Overview is intended to provide non-limiting examples of the present teachings—it is not intended to provide an exclusive or exhaustive explanation. The Detailed Description below is included to provide further information about the present systems, kits and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in this patent document.

Figure 1:
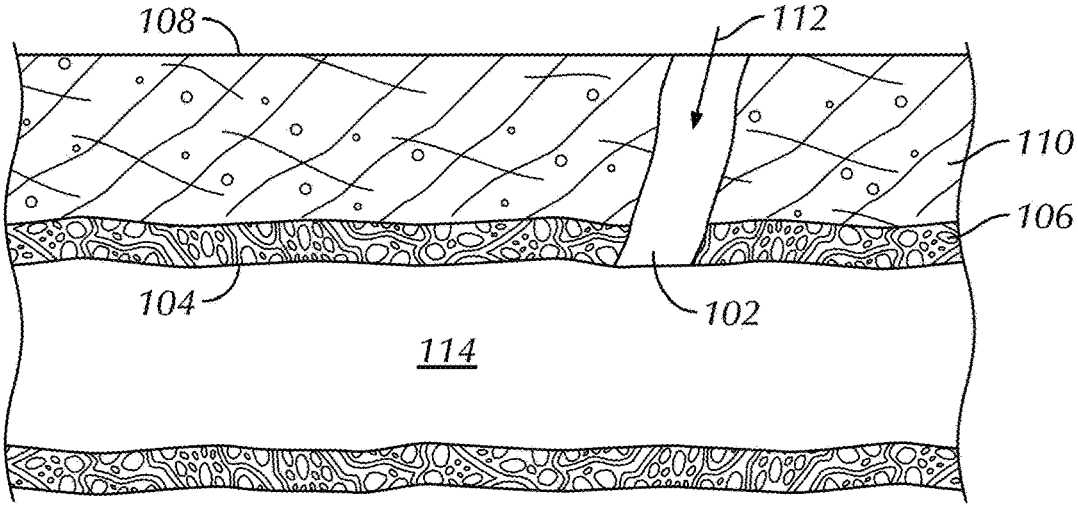
FIG. 1 is a schematic illustration of a punctured wall of a blood vessel, such as an artery.

The drawing figures are not necessarily to scale. Certain features and components may be shown exaggerated in scale or in schematic form, and some details may not be shown in the interest of clarity and conciseness.

DETAILED DESCRIPTION

Definitions

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "bioabsorbable," "biodegradable," and "bioresorbable" refer to the ability of a material to disintegrate or degrade so that no material remains after a predetermined period of time, such as after 1 week, after 5 years, or any period of time therebetween.

The terms "distal" and "proximal" refer to a position or direction relative to a treating clinician. "Distal" and "distally" refer to a position that is distant, or in a direction away, from the clinician. "Proximal" and "proximally" refer to a position that is closer to, or in a direction toward, the clinician.

The terms "inner surface" and "outer surface" refer to bodily tissue surfaces near a puncture or other opening. The term "inner surface" refers to an intra-luminal surface of a wall of a blood vessel or a wall of a body cavity. The term "outer surface" refers to an extra-luminal surface of a wall of a blood vessel or a wall of a body cavity. When the puncture or other opening is a septum between two body cavities or a biopsy tract, the "outer surface" is the surface proximal to a treating clinician, and the "inner surface" is the surface distal to the clinician. The terms "patient" and "subject" refer to mammals and include both humans and animals.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Example Applications of the Present Teachings

Vascular procedures are performed throughout the world and require access to a blood vessel of the vasculature system through a puncture. FIG. 1 is a schematic illustration of a puncture 102 in a wall 104 of a blood vessel 106 (e.g., a femoral artery). The vessel 106 is shown in cross-section passing beneath skin 108 and subcutaneous tissue 110 of a patient. The vessel 106 has been accessed by way of a percutaneous surgical procedure, which has resulted in an access path 112 consisting of a tissue tract and the puncture 102. For example, the tract and puncture 102 may have resulted from inserting an introducer assembly into a lumen 114 of the vessel 106.

The present closure systems, kits and methods can be used to seal a puncture or another opening in a vessel wall, body cavity, or biopsy tract that has been created intentionally or unintentionally during a surgical procedure. Punctures made intentionally include vascular punctures made in various types of vascular, endoscopic or orthopaedic surgical procedures, or punctures made in any other type of surgical procedure, in coronary or peripheral arteries and veins, or in a body cavity. Such procedures include angiographic examination, angioplasty, laser angioplasty, valvuloplasty, atherectomy, stent deployment, rotablator treatment, aortic prosthesis implantation, aneurysm repair, ventricular-assist device deployment, intraortic balloon pump treatment, pacemaker implantation, any intra-cardiac procedure, electrophysiological procedures, interventional radiology, and various other diagnostic, prophylactic, and therapeutic procedures such as dialysis and procedures relating to percutaneous extracorporeal circulation.

Figure 2:
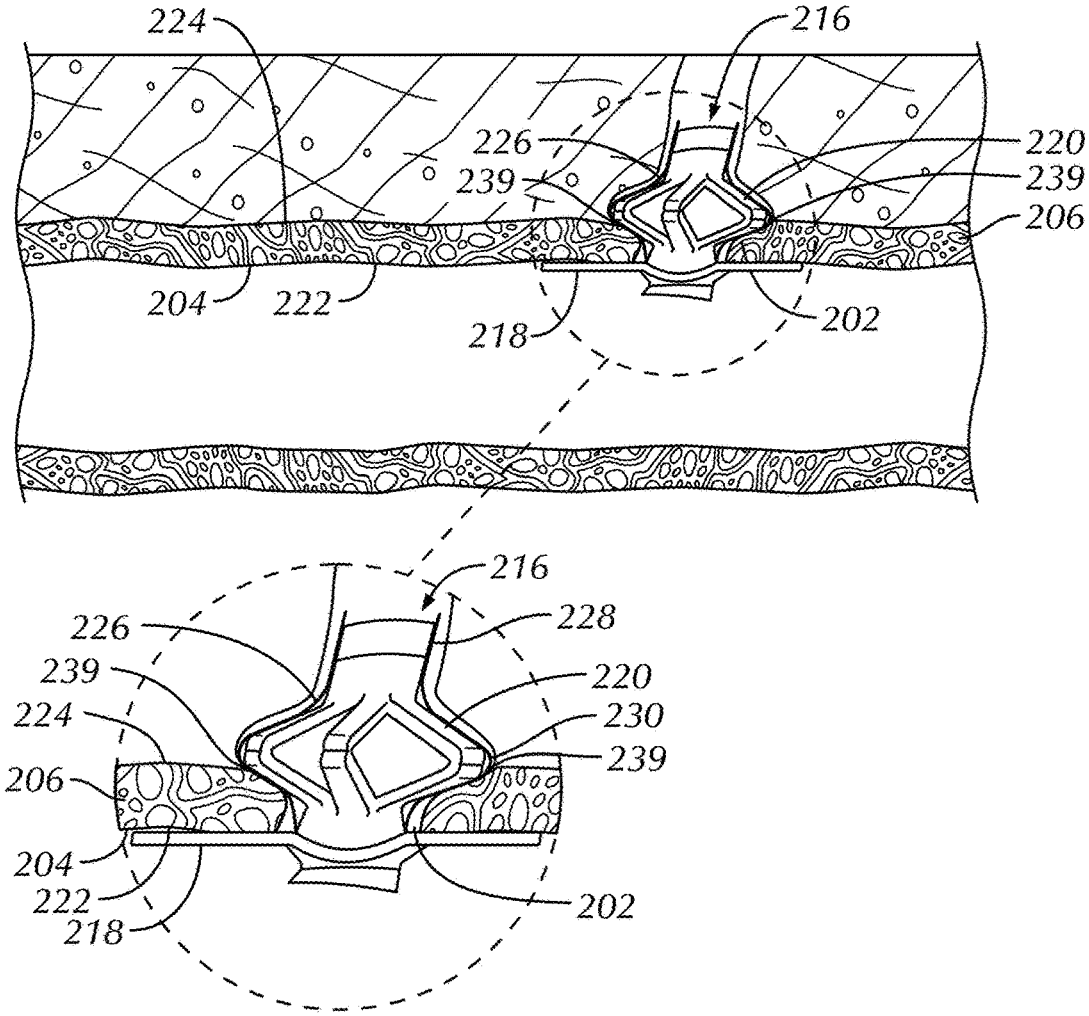
FIG. 2 is a schematic illustration of an implant assembly sealing a punctured wall of a blood vessel, as constructed in accordance with at least one embodiment of the present teachings.

Implant Assembly:

FIG. 2 is a schematic illustration of an implant assembly 216 in its fully deployed configuration and sealing a puncture 202 in a wall 204 of a vessel 206, as constructed in accordance with at least one embodiment. Sealing can be achieved by respectively applying inner 218 (intra-luminal) and outer 220 (extra-luminal) members of the implant assembly 216 against inner 222 and outer 224 vessel wall surfaces surrounding the puncture 202. The inner member 218 can be pulled against the inner surface 222 of the vessel wall 204, and the outer member 220 can be pushed against the outer surface 224 of the vessel wall 204 so that the puncture 202 is contained or sandwiched between the members. Alternatively, the outer member 220 can be deployed such that it expands between the inner 222 and outer 224 surfaces of the vessel wall 204 or at a position spaced from the outer surface 224 of the vessel wall 204.

The implant assembly 216 can also include a sealing membrane 226 that extends from the inner member 218 and is configured at its proximal end 228 to receive the outer member 220, which can expand to a sealing circumference larger than that of the puncture 202. The presence of the sealing membrane 226 allows the implant assembly 216 to be used to seal various puncture sizes, including small, medium and large punctures resulting from 8F-24F introducer sheaths, for example. Based on the position of the outer member 220 within the sealing membrane 226 and the expandability of the outer member, the material of the sealing membrane in its mid-region 230 can be caused to expand and conform to edges 239 of the puncture 202.

All components of the implant assembly 216 can be made to be bioabsorbable. This ensures that the implant assembly 216 is absorbed into the patient after a predetermined period of time that is sufficient to permit biological repair of the vessel wall 204 and the tissue around the puncture 202. The implanted components should remain intact and slowly absorb or melt away, with no pieces coming loose and entering the blood stream. Further, it is desirable that the components initially maintain their strength and integrity so that the puncture 202 in the vessel wall 204 can begin to heal prior to the components beginning to weaken and absorb into the body.

Bioabsorbable polymers, such as polylactic acid (PLA), polyglycolic acid (PGA), trimethylene carbonate (TMC) and caprolactone (CL) can be used to form one or more of the components. Other suitable bioabsorbable polymers include, but are not limited to, poly D,L-lactide acid (PDLA), poly-L-lactic acid (PLLA), polyethylene glycol (PEG), polylactide-co-glycol acid (PLGA), polyanhydrides, polyorthoesters, polyethylene oxide (PEO), polydioxanone (PDS), polypropylene fumarate, polyethyl glutamate-co-glutamic acid, polytert-butyloxy-carbonylmethyl glutamate, polycaprolactone co-butylacrylate, polyhydroxybutyrate (PHBT) and copolymers of polyhydroxybutyrate, polyphosphazene, poly(D,L-lactide-co-caprolactone) (PLA/PCL), poly(glycolide-co-caprolactone) (PGA/PCL), polyphosphate ester, poly amino acid and polyhydroxy butyrate, polydepsipeptides, maleic anhydride copolymers, polyphosphazenes, polyiminocarbonates, poly[(97.5% dimethyltrimethylene carbonate)-co-(2.5% trimethylene carbonate)], cyanoacrylate, polycyanoacrylates, polyethylene oxide, hydroxypropyl-methylcellulose, polysaccharides (such as hyaluronic acid, chitosan and regenerate cellulose), and proteins (such as gelatin and collagen). These polymers can have a structure this is amorphous and can include a glass transition temperature that is close to the natural temperature of the body.

The components of the implant assembly 216 can optionally be designed to provide the strength and absorbtion rate desired through the use of material combinations, overmolding or other coating techniques. The entire implant assembly 216 or specific portions of one or more of its components can be over molded, coated, or otherwise incorporate a second, third, etc. material to alter its strength or absorbtion profile. In an example, the second material can be an alkaline earth metal, such as magnesium. It is believed that the combination of a magnesium material and an acidic polymer (e.g., PLA) can allow for tailoring the speed of component decay. It has been observed that magnesium does not dissolve in an environment having a pH above about 8, but degrades relatively rapidly at a pH of about 7.4 to 7.6.

The acidic nature of the polymer can maintain the pH in the vicinity of the magnesium below a critical level, such as below 8, thereby encouraging degradation.

Figure 3:
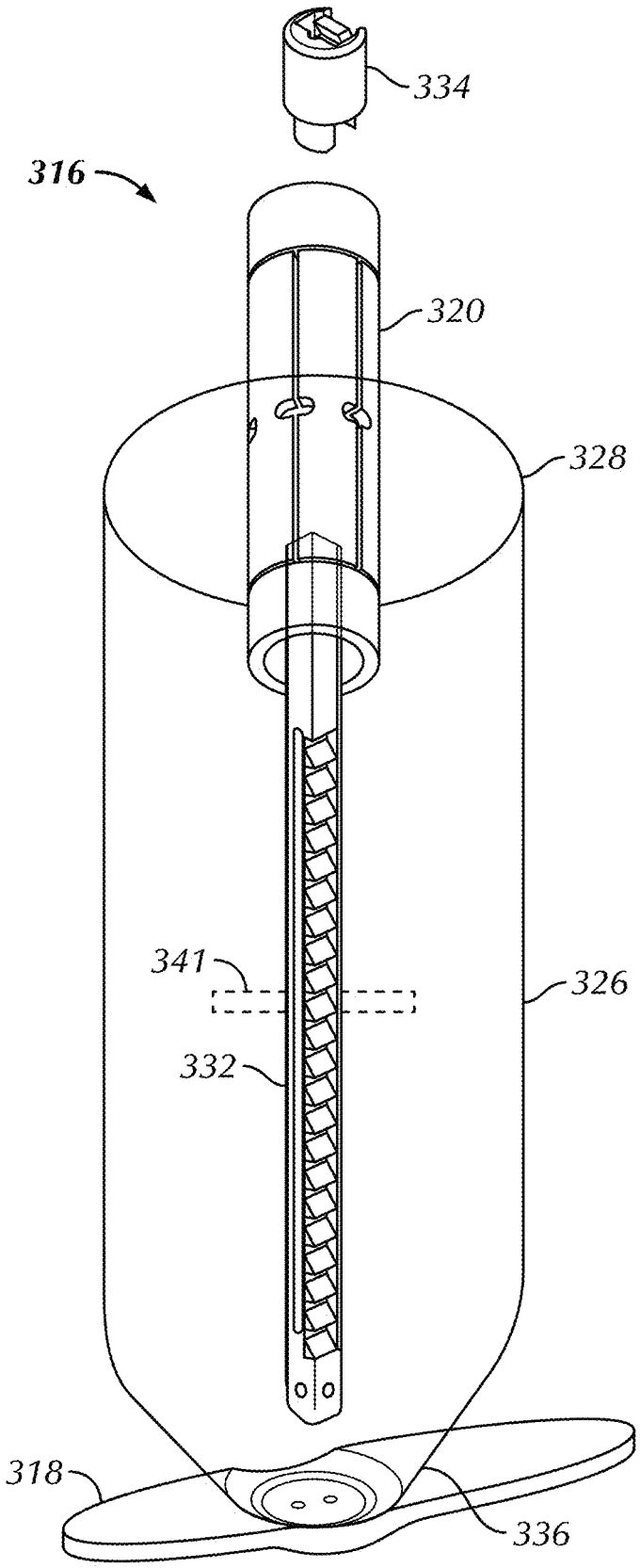
FIG. 3 is an exploded illustration of an implant assembly, as constructed in accordance with at least one embodiment of the present teachings.

FIG. 3 is an exploded view of an implant assembly 316, as constructed in accordance with at least one embodiment. The implant assembly 316 can comprise three primary components, namely, an inner member 318, a sealing membrane 326 and an outer member 320. The implant assembly 316 can further comprise a connecting member 332, which can optionally be incorporated into the inner member 318, and a locking member 334, which can optionally be incorporated into the outer member 320.

Figure 11A:
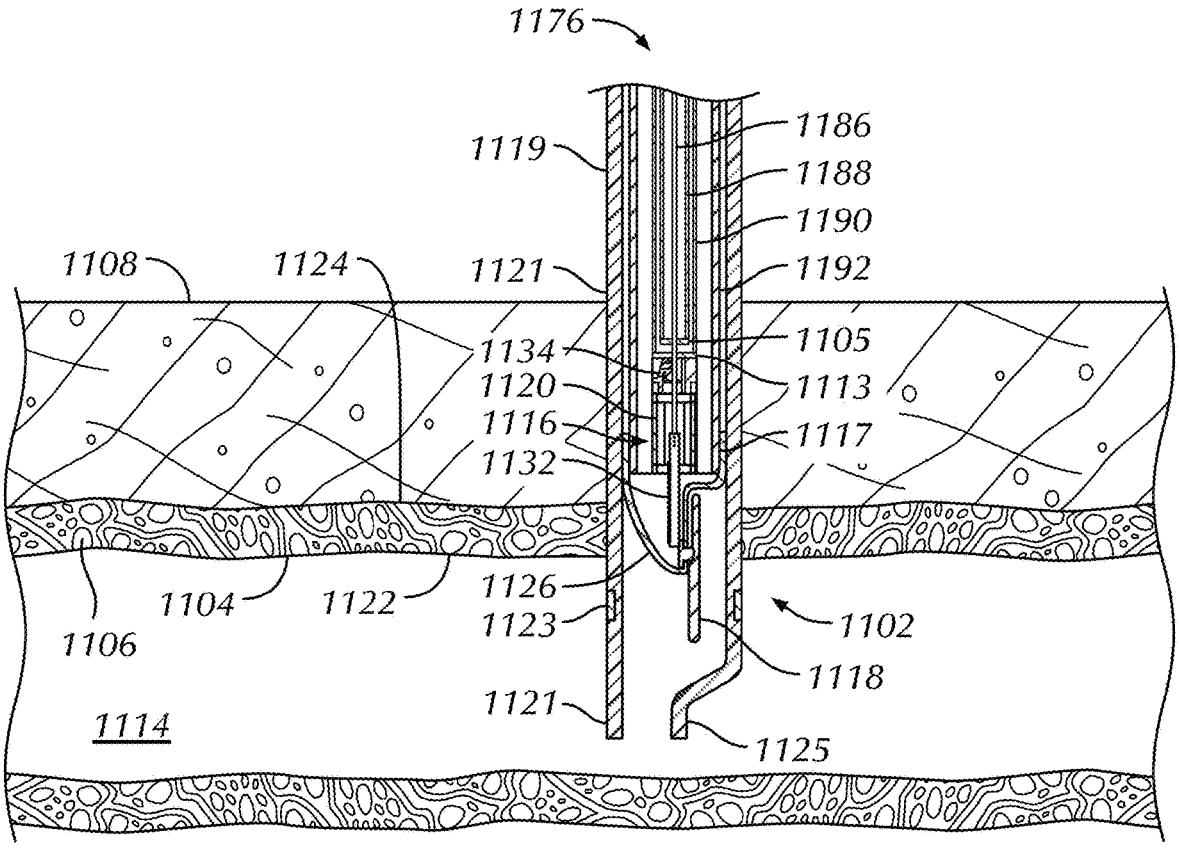
FIGS. 11A-11C are schematic illustrations, in sequential order, of an introducer sheath and a delivery assembly delivering and deploying an implant assembly at a puncture site, as constructed in accordance with at least one embodiment of the present teachings.
Figure 11B:
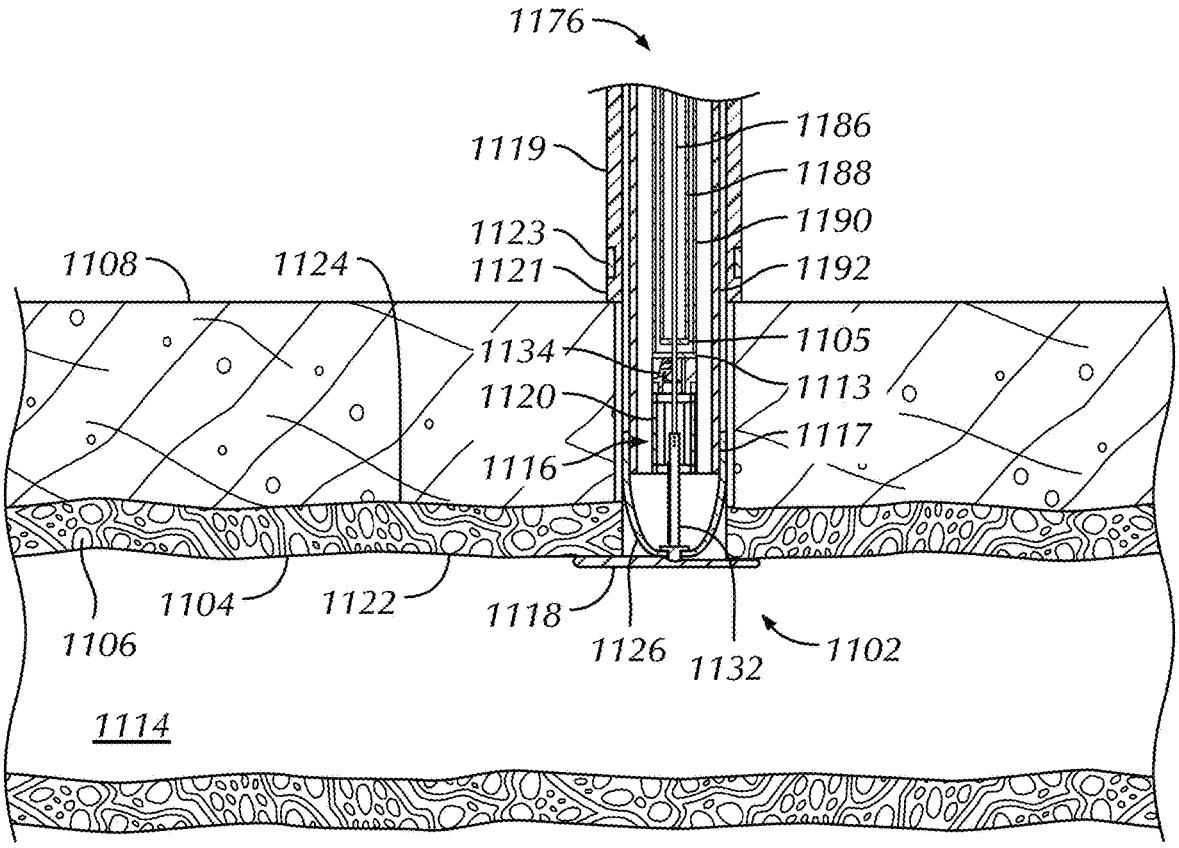
Figure 11C:
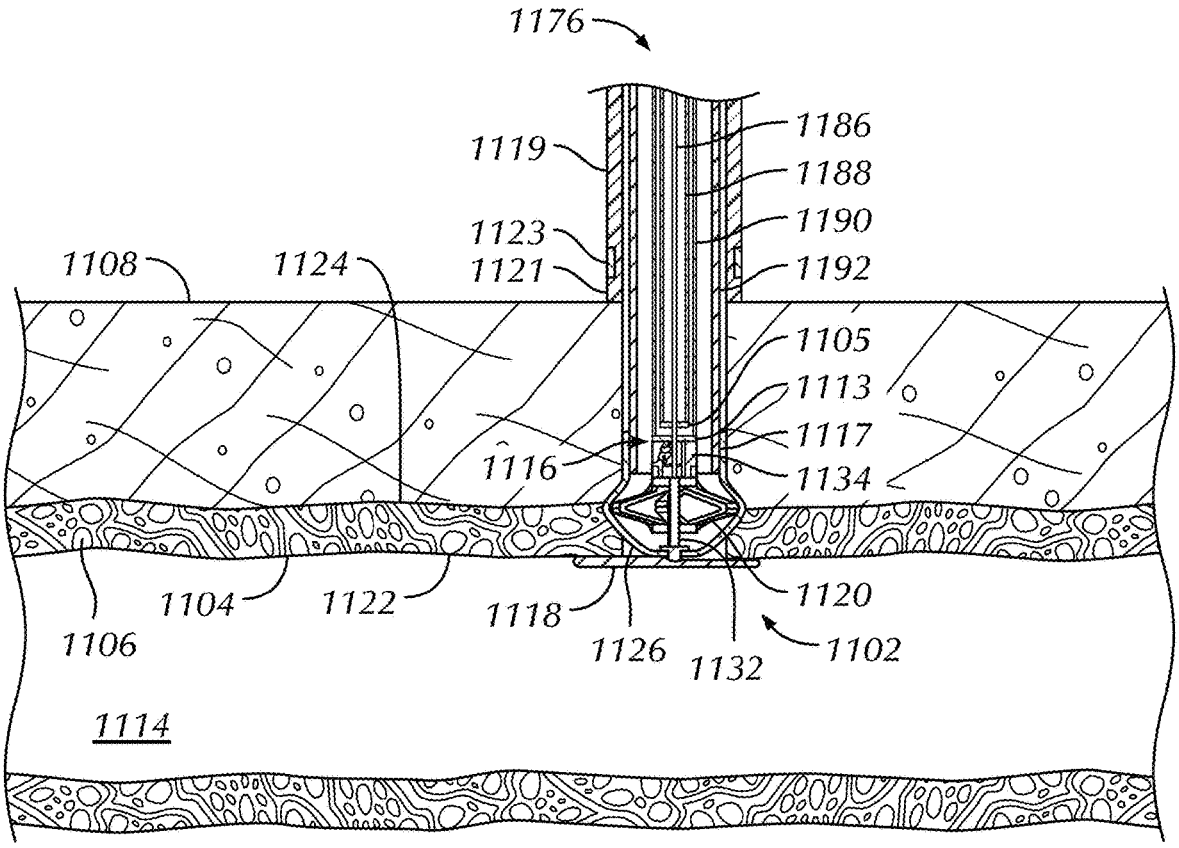

In use, the components of the implant assembly 316 can be placed and assembled in a distal-to-proximal manner (see, e.g., FIGS. 11A-11C). The inner member 318 can first be inserted through a puncture in a wall of a vessel and introduced into a lumen of the vessel. The inner member 318 can then be retracted until it is in contact with an inner surface of the vessel wall. The connecting member 332 and the sealing membrane 326 can extend through the puncture, and the connecting member 332 can be used to hold the inner member 318 against the inner surface of the vessel wall. The outer member 320—illustrated in its undeployed, delivery configuration—can then be received by the sealing membrane 326—which can be in the form of a generally elongated tubular body with a closed or sealed distal end 336 and an open proximal end 328—and advanced along the connecting member 332 until it contacts the outer surface of the vessel wall or until it contacts a stop member 341 placed along the length of the connecting member 332. The stop member 341 can provide a predetermined stop of the outer member 320 for closure of punctures such as apical access for mitral valve replacement in which there is a relatively long path to seal. Tension can be maintained on the connecting member 332 and a pushing force can be applied to the outer member 320 to expand its delivery configuration to a sealing configuration. Once the outer member 320 has achieved a longitudinally-compressed and transversely-expanded state, the locking member 334 can be secured to the connecting member 332. In other examples, the proximal end 328 can have a closed or sealed proximal end 328 and the outer member 320 can be urged against the closed end.

Figure 4:
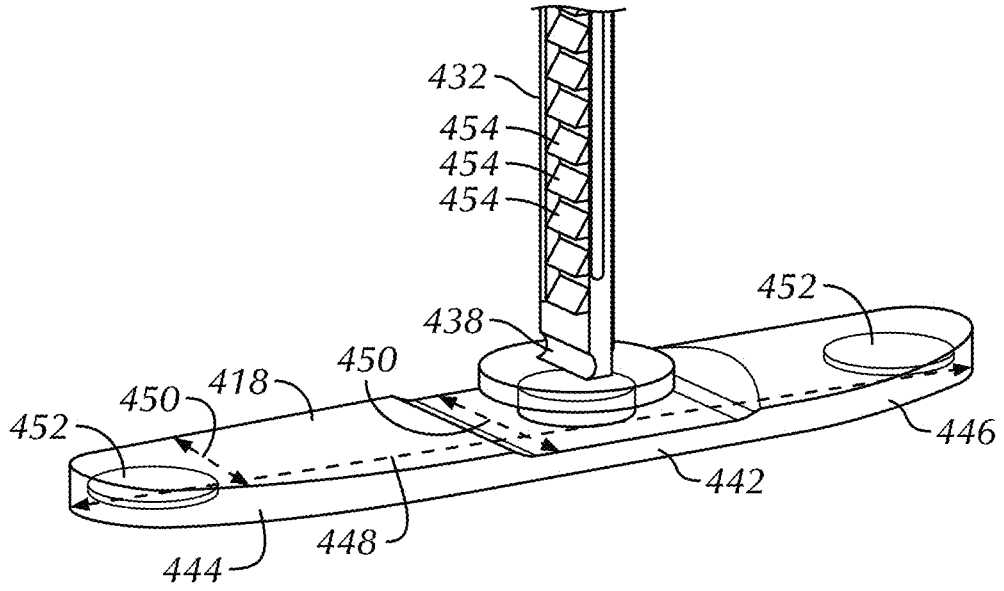
FIGS. 4 and 5 are schematic illustrations of an inner member and a connecting member in a deployed orientation, as constructed in accordance with at least two embodiments of the present teachings.
Figure 5:
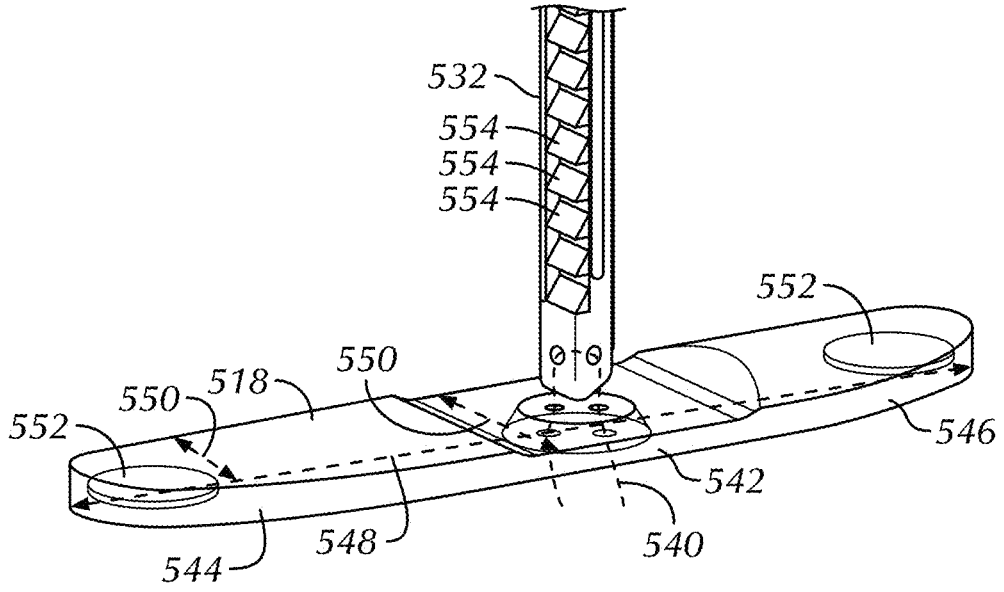

Inner Member and Connecting Member of Implant Assembly:

FIGS. 4 and 5 are schematic illustrations of an inner member 418, 518 and a connecting member 432, 532, as constructed in accordance with at least two embodiments. The connecting member 432, 532 can be a stem, rod, tube, string, thread or other filament that is part of the inner member 418, 518, or can be a stem, rod, tube, string, thread or other filament that is attached to the inner member 418, 518. FIG. 4 illustrates a configuration in which the inner member 418 and the connecting member 432 are combined into a single molded piece. A hinge 438 can be incorporated at the base of the connecting member 432 to allow the connecting member to bend or otherwise reorientate with respect to the inner member 418. This bending can be beneficial when delivering the inner member 418 through an introducer sheath and puncture, as illustrated in FIG. 11A. In an example, the hinge 438 can be formed by notching the base of the connecting member 432. FIG. 5 illustrates a configuration in which the inner member 518 and the connecting member 532 are separate, but attachable pieces. In an example, the connecting member 532 can be attached to the inner member 518 using a dissolvable suture 540, a mechanical fastener, adhesive or any other suitable joining means. When formed separately, the inner 518 and connecting 532 members may or may not be comprised of the same bioabsorbable material or material combination.

The inner member 418, 518 can be configured to be extended through a puncture in a wall of a vessel and into a lumen of the vessel to at least partially block the internal opening of the puncture. As illustrated in FIGS. 4 and 5, the inner member 418, 518 can have an enlarged central region 442, 542, positioned between first 444, 544 and second 446, 546 end regions, where it attaches to the connecting member 432, 532. This enlarged region 442, 542 can provide a sufficient area to cover the internal opening of the puncture. A longitudinal axis 448, 548 can define a lengthwise dimension and transverse axes 450, 550 can define widthwise dimensions. The lengthwise dimension can range from about 10 mm to about 20 mm, for example. The widthwise dimension at the end regions can range from about 3 mm to about 5 mm, for example. At the enlarged region 442, 542, the widthwise dimension can progressively increase so that its maximum width ranges from about 4 mm to about 8 mm, for example.

The inner member 418, 518 can be composed of a thin, narrow strip or bar of material that is sufficiently rigid to be resistant to deformation, yet thin enough to conform to the inner surface of the vessel wall and not take up a substantial portion of the lumen of the vessel. It can be important for the inner member 418, 518 to be resistant to deformation to preclude it from bending and passing back through the puncture in which it was introduced. It can also be important that in its final in situ position, as illustrated in FIG. 2, the inner member 418, 518 does not block or otherwise impede the flow of blood through the vessel. Since the component can be formed of a resorbable material, it can be left in pace within the body until it is absorbed.

The inner member 418, 518 can be asymmetrically-shaped and include radiopaque marking elements 452, 552 to help a treating clinician position it within a vessel. For example, the inner member 418, 518 can include a first end region 444, 544 that is longer than a second end region 446, 546 to encourage pivoting about its attachment location to the connecting member 432, 532 when deployed from an introducer sheath. In the embodiment shown, the first end region 444, 544 can be about ⅓ longer than the second end region 446, 546. The inner member 418, 518 can also include the radiopaque marking elements 452, 552 or a coating that is viewable on x-ray making visualization during delivery and deployment possible. The radiopaque material can be sodium diatrizoate, iopamidol, iohexol, iodixanol, iopromide, or another water soluble material, for example, and can be added to the material or material combination from which the inner member is composed or encapsulated in one or more pockets therein. In an example, the radiopaque marking elements 452, 552 are encapsulated within each of the first 444, 544 and second 446, 546 end regions of the inner member 418, 518. In other examples, the radiopaque material can be non-water soluble, such as tungsten and platinum, and in the form of particles, washers, or wires (longitudinal or circumferential).

The connecting member 432, 532 can have a length and cross-sectional size that allows it to fit through the puncture of the vessel wall. It can be desirable for the connecting member to have a length of at least about 38 mm (pre-cut) and at least about 9 mm (post-cut), such as between about 5 mm and about 60 mm, for example. The connecting member 432, 532 can have a constant or varying cross-sectional size. The connecting member 432, 532 can have a perpendicular or angled orientation relative to the inner member 418, 518 in the absence of external forces (e.g., delivery forces from a wall of an introducer sheath).

A number of pawls 454, 554 or other spaced elements can be formed on an outer surface of the connecting member 432, 532. The pawls 454, 554 can be spaced from each other in the longitudinal direction of the connecting member 432, 532. The presence of these spaced pawls 454, 554 can allow for adjusting the distance between a proximal end of an outer member (see, e.g., FIGS. 7A and 7B) and a proximal end of the inner member 418, 518. For example, during deployment of an implant assembly at a puncture site, the outer member can be pushed against the outer surface of the vessel wall or a stop member (see, e.g., element 341 of FIG. 3) by urging the proximal end of the outer member in a distal direction toward the proximal end of the inner member 418, 518. A locking member (see, e.g., FIGS. 8A and 8B) can provide resistance and prevent the proximal end of the outer member from retracting proximally and disengaging from the vessel wall or stop member.

Figure 6:
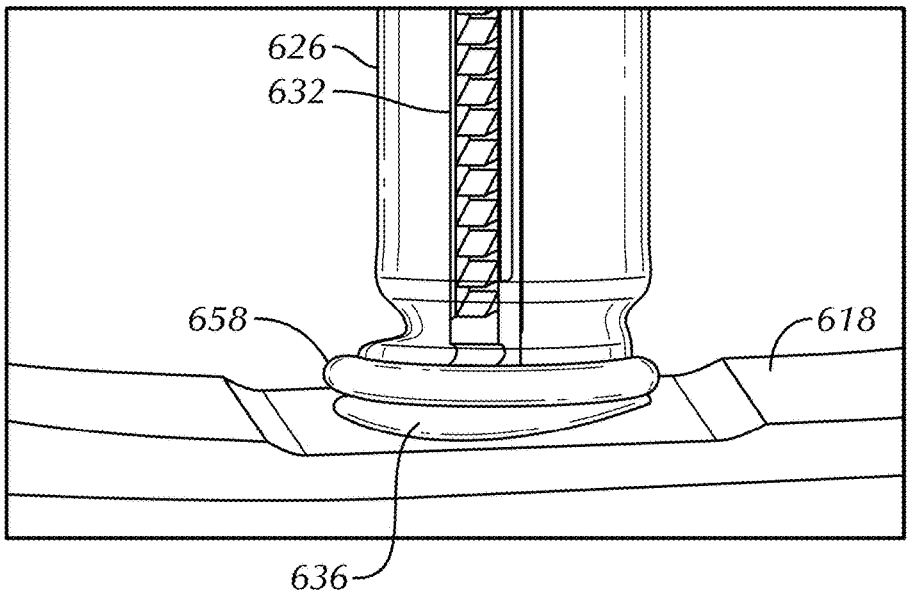
FIG. 6 is a schematic illustration of a sealing membrane attached to an inner member and surrounding portions of a connecting member, as constructed in accordance with at least one embodiment of the present teachings.

Sealing Membrane of Implant Assembly:

FIG. 6 is a schematic illustration of a sealing membrane 626 attached to an inner member 618 on its distal end 636 and surrounding portions of a connecting member 632 along its mid-region and proximal end portions, as constructed in accordance with at least one embodiment. In use, the distal end 636 of the sealing membrane 626 can be located within or near an inner surface of the puncture, while the proximal end can be located outside of an outer surface of the puncture and can include an opening through which an outer member can be received. When using the inner member embodiment illustrated in FIG. 4, the distal end of the sealing membrane can be slid over a boss on an upper surface of the inner member 618 and pinched in an undercut section using an absorbable suture or O-ring 658, for example. When using the inner member embodiment illustrated in FIG. 5, the distal end 636 of the sealing membrane 626 can be inserted through a center hole of the inner member 618 and pinched in placed by a tapered plug member. Alternatively or conjunctively, the sealing membrane 626 can be secured to the inner member 618 using a medical-grade adhesive, thermal or solvent bonding, or any other suitable joining means.

The sealing membrane 626 can be formed of a flexible, fluid impermeable and biodegradable polymer having an inner diameter or about 2 mm or more, a wall thickness in a range of about 0.025 mm to about 0.38 mm, and which can be cut to have a length of at least about 10 mm, for example. In an example, the sealing membrane 626 is formed of STRATAPRENE® 3534 copolymer material, which is commercially available from Poly-Med, Inc., of Anderson, S.C. Because the sealing membrane 626 can be constructed from a flexible material, it is capable of expanding and contracting to accommodate changes in the size and shape of the outer member (e.g., during its change from a delivery configuration to a sealing configuration). In addition, because the outer member is larger than the diameter of the puncture in its deployed, sealing configuration, the mid-region of the sealing membrane 626 can continuously remain in contact with edges of the puncture and prevent blood leakage.

Figure 7A:
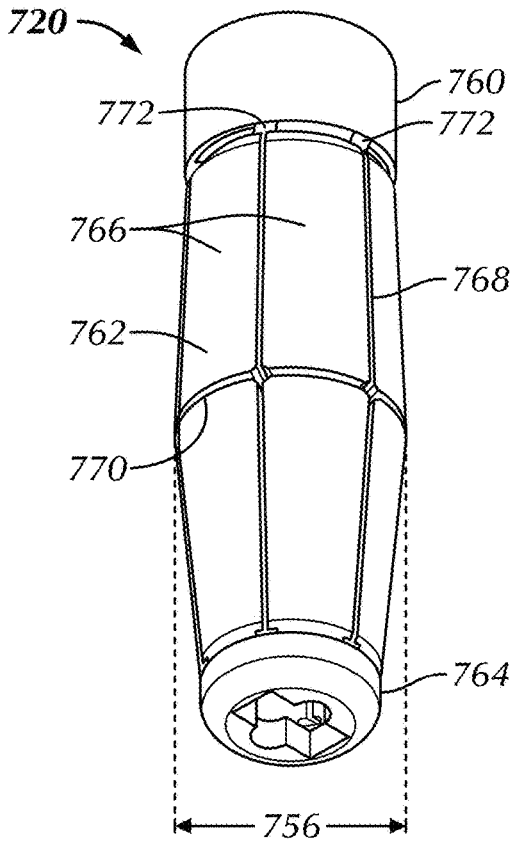
FIGS. 7A and 7B are schematic illustrations of an outer member receivable within a sealing membrane and expandable from a delivery configuration to a sealing configuration, as constructed in accordance with at least one embodiment of the present teachings.
Figure 7B:
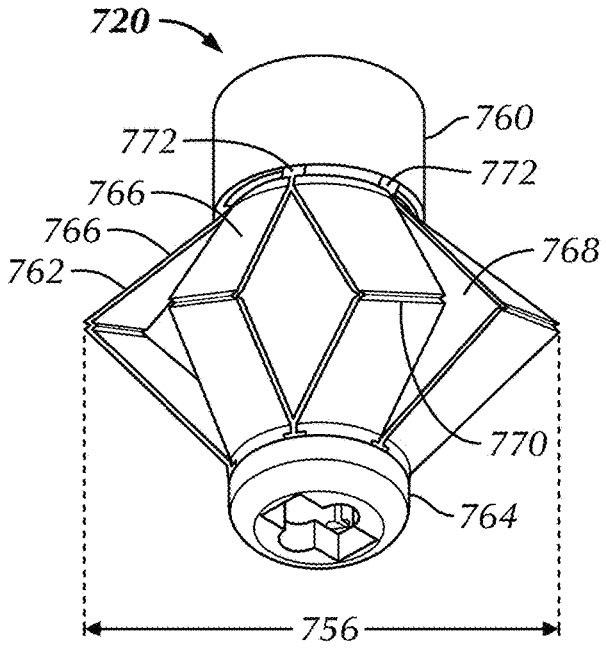

Outer Member of Implant Assembly:

FIGS. 7A and 7B are schematic illustrations of an outer member 720 that can be expanded from a delivery configuration (FIG. 7A) to a sealing configuration (FIG. 7B), as constructed in accordance with at least one embodiment. The low profile of the delivery configuration can be useful to facilitate delivery of the outer member 720, while the sealing configuration can be useful to facilitate firmly lodging the outer member 720 in a tissue tract and sealing a puncture against outward blood flow. In an example, a diameter 756 of the outer member 720 in the sealing configuration (FIG. 7B) is at least three times the diameter 756 of the outer member 720 in the delivery configuration (FIG. 7A). This can allow the outer member 720, when in the sealing configuration, to cover the puncture and neighboring portions of the puncture from outside of the blood vessel wall.

The outer member 720 can be formed from a substantially rigid body with a generally cylindrical or polygonal (e.g., square or hexagonal) shape and having a proximal end 760, an intermediate deformation portion 762, and a distal end 764. The body can have a pre-expanded, delivery length between about 6 mm and about 20 mm, and a pre-expanded, delivery diameter between about 2.5 mm and 20 mm, for example. Other shapes and dimensions are also possible.

The intermediate deformation portion 762 of the outer member 720 can include support struts 766 created by parallel slits or cuts 768 completely or partially through the wall of the member. The center portions of the support struts 766 can move radially outward in a hinge-like manner in response to the movement of the member's proximal end 760 toward its distal end 764. In the delivery configuration, the struts 766 of the intermediate deformation portion 762 can be elongated in a direction substantially perpendicular to an in situ inner member, while in the sealing configuration, the struts 766 can be contracted in a direction substantially parallel to the in situ inner member. A hinge 770 near the center of the struts 766 can be formed in a variety of ways, including mechanical thinning, denting, grinding, heat forming or machining, or a weakened section created by micro cuts or tapered grooves. The number, length and distance between the slits or cuts 768 can affect both the anchorability of the outer member 720 and the collapsibility of the member. As an alternative to parallel slits or cuts 768, the slits or cuts can be helical or serpentine such that they are adapted to expand and form wings upon rotation of the member's proximal end 760 relative to its distal end 764.

The slits or cuts 768 in the intermediate deformation portion 762 of the outer member 720 can be formed using an etching or cutting process. For example, the slits can be cut along the intermediate portion of the rigid body using a cutting tool, such as a razor blade. According to some embodiments, the slits are cut without removing any significant amount of material from the rigid body, i.e., the formation of the slits does not significantly reduce the overall volume of rigid body. According to other embodiments, the slits are formed by cutting material out of the rigid body such that its volume is reduced.

One or both ends 772 of each slit 768 can be rounded so-as-to relieve stresses at the axial ends of the slit. This can prevent the slits from lengthening due to stress. In embodiments where the slits are cut without removing any significant amount of material from the rigid body, rounded ends can be produced by burning holes at both ends of each slit. In embodiments where the slits are formed by cutting material out of the rigid body, rounded ends can be formed during the cutting process. The size of the rounded ends can vary depending upon the dimensions of the rigid body and the amount of stress release required.

The outer member 720 can be disposed within the lumen of a sealing membrane and received over and slid along a connecting member so that the distance between the outer member and the inner member is adjustable in an aligned manner, depending on a puncture or opening to be sealed. This makes it possible to cope with a variety of situations or cases, such as a patient with a thick, thin, hard or soft in vivo vessel wall. During expansion of the outer member 720 to its sealing configuration, the sealing membrane can exert counteractive or countervailing contractile forces on the outer member. In this way, the sealing membrane does not expand passively, but rather, the outer member 720 forcibly expands the sealing membrane to cause the membrane to be taunt and capable of sealing the puncture in a fluid tight manner. Alternatively, the sealing membrane can be sized and shaped such that the outer member 720 expands to its sealing configuration to fill the space within the sealing membrane.

Although not shown, it is contemplated that more than one outer member 720 can be used, such as in a stacking arrangement. In such an example, the expanded diameters of the outer members 720 can decrease in size as the distance from the treatment site (e.g., vessel wall puncture) increases.

Figure 8A:
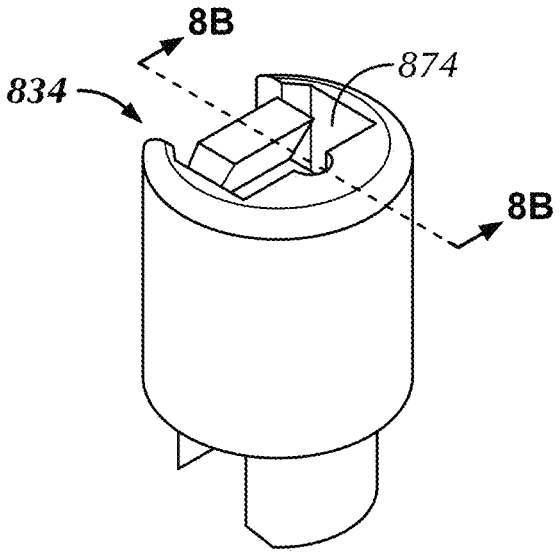
FIGS. 8A, 8B and 9 are schematic illustrations of a locking member that can be received by a proximal end of a connecting member, as constructed in accordance with at least two embodiments of the present teachings.
Figure 8B:
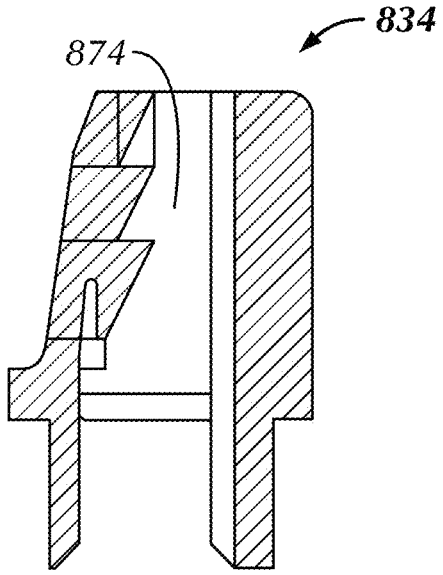
Figure 9:
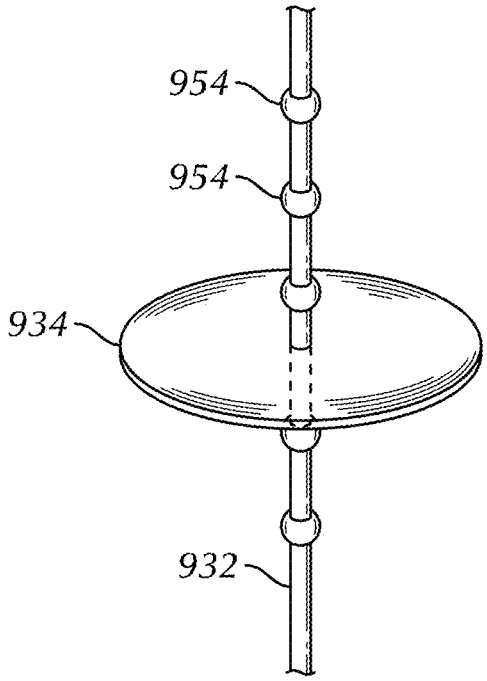

Locking Member of Implant Assembly:

FIGS. 8A, 8B and 9 are schematic illustrations of a locking member 834, 934 that can be received by a proximal end of a connecting member 932, as constructed in accordance with at least two embodiments. The locking member 834, 934 can be slid along the connecting member and into abutment against a proximal end of an outer member, thereby maintaining an in situ position of an inner member against an inner surface of a vessel wall, an expanded configuration of an outer member against an outer surface of the vessel wall or a stop member (see, e.g., element 341 of FIG. 3), and contact between a sealing membrane and edges of a puncture (as illustrated in FIG. 2) or tissue tract. Portions of the connecting member proximal to the locking member can be cut using a mechanical means (e.g., shearing arrangement) or thermal means and removed after the locking member 834, 934 has been secured to the connecting member.

The locking member 834, 934 can take a variety of forms, non-limiting examples of which are provided in FIGS. 8A, 8B and 9. One skilled in the art will recognize that the locking member 834, 934 can assume numerous other configurations while retaining its capability to maintain a position of the inner and outer members. FIGS. 8A and 8B illustrate a configuration in which the locking member 834 comprises a notched passageway 874 that is slidable and receives a number of pawls or other spaced elements formed on an outer surface of the connecting member in one direction, but is resistant to sliding of the pawls or other spaced elements in a second, opposite direction. FIG. 9 illustrates a configuration in which the locking member 934 comprises a compressible disk that is slidable and receives a connecting member 932 in the form of a filament having a plurality of ball projections 954 thereon. Upon the application of sufficient pulling force to the filament, one or more ball projections 954 can pass through a central lumen of the disk to lock a position of the filament.

While FIGS. 8A, 8B and 9 illustrate distinct locking members, the locking member can optionally be integrated into a portion of the outer member, such as at its proximal end.

Figure 10A:
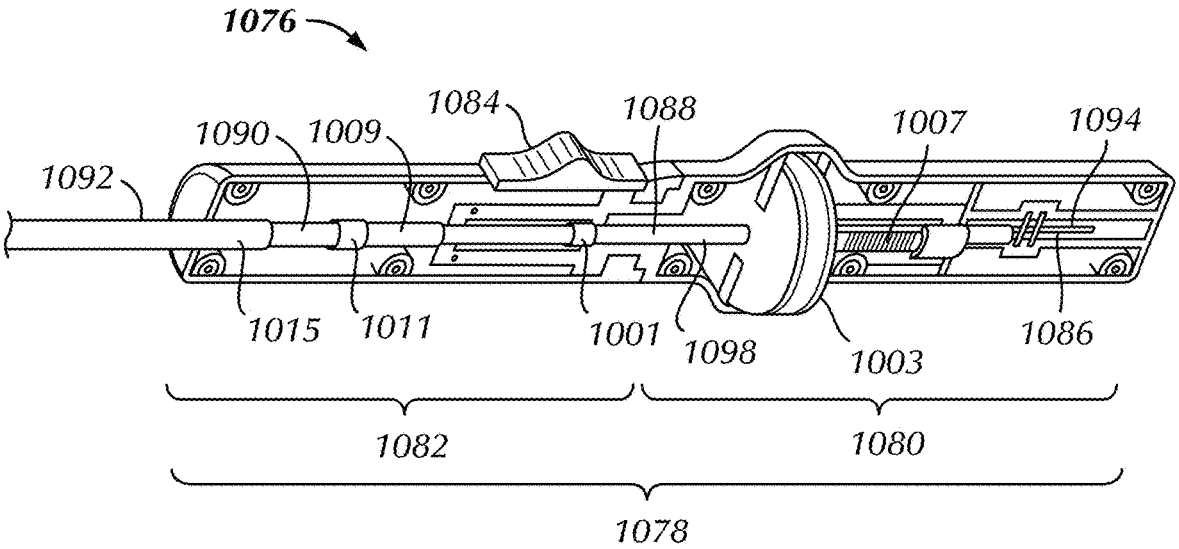
FIG. 10A is a schematic cross-sectional illustration of a proximal portion of a delivery assembly configured to deliver and deploy an implant assembly at a puncture site, as constructed in accordance with at least one embodiment.
Figure 10B:
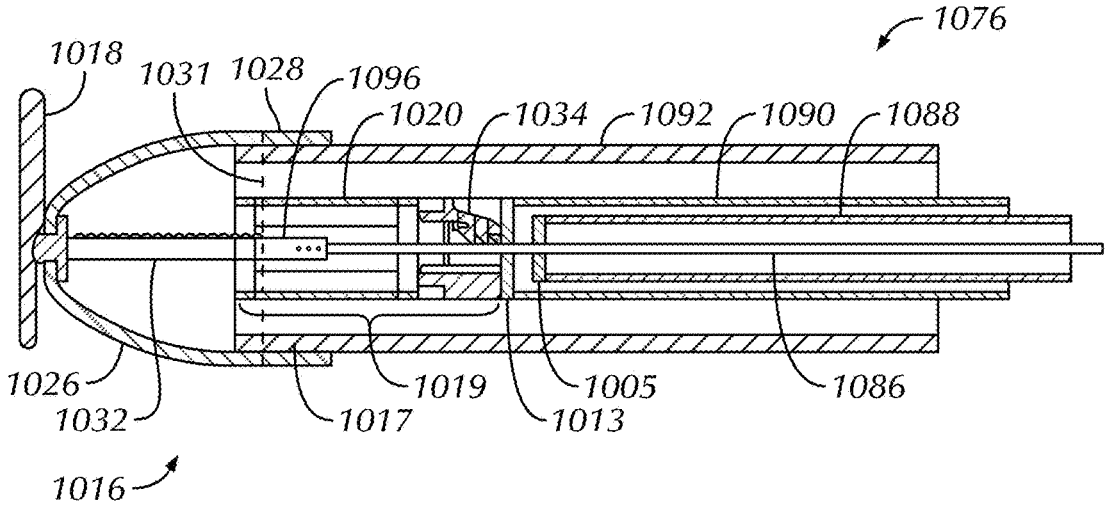
FIG. 10B is a schematic cross-sectional illustration of an implant assembly mounted on a distal portion of a delivery assembly, as constructed in accordance with at least one embodiment.

Delivery Assembly:

FIG. 10A is a schematic cross-sectional illustration of a proximal portion of a delivery assembly 1076 configured to deploy an implant assembly at a puncture site, as constructed in accordance with at least one embodiment. FIG. 10B is a schematic cross-sectional illustration of an implant assembly 1016 mounted on a distal portion of the delivery assembly 1076, as constructed in accordance with at least one embodiment.

The delivery assembly 1076 can extend from a handle 1078, operable by a treating clinician, at its proximal portion to connections with components of the implant assembly 1016 at its distal portion. The handle 1078 can include a proximal housing portion 1080 and a distal housing portion 1082. A handle lock 1084, which can be activated during initial delivery steps, prevents relative movement between the two housing portions 1080, 1082. When the lock 1084 is not activated, the two housing portions 1080, 1082 can be rotated relative to one another.

Four elongate members can extend distally from the handle 1078 to the implant assembly 1016, namely (moving from inside-out), a rail 1086, a shear tube 1088, a push tube 1090, and a delivery tube 1092.

The rail 1086 and the shear tube 1088 can be engaged with the proximal housing portion 1080 on their proximal ends. The rail 1086 can extend from a proximal end 1094, which is statically coupled with the proximal housing portion 1080, to a distal end 1096, which is engaged with an inner member 1018 of the implant assembly 1016. In an example, the rail 1086 can include a stainless steel ribbon having a rectangular cross-section. The proximal end of the ribbon can be secured in a rectangular pocket in the proximal housing portion 1080. The distal end of the ribbon can be molded into a proximal end of a connecting member 1032 of the implant assembly 1016. The connecting member 1032 attaches to the inner member 1018 on its distal end. The connecting member 1032 can include a rectangular cross-section slightly larger than that of the rail 1086. The shear tube 1088 can extend from a proximal end 1098, which is engaged with an axial tract 1001 and an actuation member 1003 of the proximal housing portion 1080, to a distal end 1005, which includes a keyed passageway and abuts locking 1034 and outer 1020 members of the implant assembly 1016. The axial tract 1001 can ensure that the shear tube 1088 can only move axially relative to the proximal housing portion 1080, with such axial movement being created through movement of the actuation member 1003. In an example, the actuation member 1003 includes a rotatable knob engaged with a threaded shaft 1007. Rotation of the knob in a first direction urges distal movement of the threaded shaft 1007. The distal movement of the threaded shaft 1007 causes distal movement of the shear tube 1088, which can transfer such movements (via push tube 1090) to the locking 1034 and outer 1020 members of the implant assembly 1016.

The push tube 1090 and the delivery tube 1092 can be engaged with the distal housing portion 1082 on their proximal ends. The push tube 1090 can extend from a proximal end 1009, which is engaged with an axial tract 1011 of the distal housing portion 1082 such that the tube can only move axially relative to the distal housing portion, to a distal end 1013, which includes a keyed passageway similar in size and shape to the keyed passageway of the shear tube 1088. The push tube 1090 surrounds portions of the shear tube 1088 and its distal end 1013 extends distal to the distal end 1005 of the shear tube. As such, when the shear tube 1088 is moved axially in a distal direction, the push tube 1090 is also moved distally. The keyed passageways of the shear 1088 and push 1090 tubes can be configured to receive and slide along the rail 1086 and the connecting 1032 member. The delivery tube 1092 can concentrically surround portions of the push tube 1090 and the shear tube 1088. On its proximal end 1015, the delivery tube 1092 can be statically coupled with the distal housing portion 1082; on its distal end 1017, an outer surface of the delivery tube 1092 can be statically coupled to a proximal end 1028 of a sealing membrane 1026 of the implant assembly 1016. Prior to distal movement of the shear 1088 and push 1090 tubes, the distal end 1017 of the delivery tube 1092 can be positioned distal to the distal ends 1005, 1013 of the shear and push tubes, thereby creating an internal cavity 1019 for placement of the locking 1034 and outer 1020 members during initial delivery. After distal movement of the shear 1088 and push 1090 tubes, the distal end 1017 of the delivery tube 1092 can be positioned proximal to the distal ends 1005, 1013 of the shear and push tubes.

The handle 1078 can include certain features to ease manufacturing and use. For example, the handle 1078 can include a clamshell-like configuration including four pieces (two for each of the proximal and distal housing portions) allowing for the placement of proximal ends of the four elongate members during manufacture.

A distal end of the handle 1078 can include engagement features (e.g., snap lock arms) configured to detachable couple to a proximal end of an introducer sheath. Further, an outer surface portion of the handle 1078 can include a flat surface, visible marking or other indicator means that conveys an orientation of the distally-positioned implant assembly 1016 to the treating clinician.

Delivery of Implant Assembly Using Introducer Sheath and Delivery Assembly:

FIGS. 11A-11C are schematic illustrations, in sequential order, of an introducer sheath 1119 and a delivery assembly 1176 delivering and deploying an implant assembly 1116 at a puncture site 1102, as constructed in accordance with at least one embodiment. The delivery assembly 1176 may take other suitable configurations, but will be described in association with the configuration illustrated and described in FIGS. 10A and 10B. A dilator (not shown) can be inserted through the introducer sheath 1119 and over a guidewire (not shown) into a vessel lumen 1114 such that portions of the introducer sheath 1119 and dilator extend through an opening in a patient's skin 1108, through a tissue tract, through the puncture 1102 and into the vessel lumen 1114. The location of the introducer sheath's distal end 1121 can be verified using a radiopaque marker band 1123 embedded or otherwise attached to the sheath. Next, the guidewire and dilator can be withdrawn, and distal portions of the delivery assembly 1176 can be inserted into a proximal end of the introducer sheath 1119 using a valve bypass (not shown) and advanced toward the distal end 1121 of the introducer sheath, as illustrated in FIG. 11A. An inner member 1118 of the implant assembly 1176 can be retained in a longitudinal, axially-aligned orientation by a wall of the introducer sheath 1119 during this advancement.

The delivery assembly 1176 can be further advanced through the introducer sheath 1119 and past its distal tip 1121 so that the inner member 1118 extends into the vessel lumen 1114. As the inner member 1118 is released from the confines of the introducer sheath 1119, it can be pivoted to a transverse orientation by way of a dimple (or concavity) 1125 at the distal end 1121 of the introducer sheath. This pivoting of the inner member 1118 can be further encouraged by an offset connection to a connecting member 1132. After the inner member 1118 is advanced past the distal end 1121 of the introducer sheath 1119 and into the vessel lumen 1114, the introducer sheath 1119 can be pulled proximally and its proximal hub can be brought into engagement with snap lock arms on a distal end of a handle of the delivery assembly 1176. This proximal pulling moves the distal end 1121 of the introducer sheath 1119 away from the vicinity of the vessel wall 1104, providing space for components of the implant assembly 1116 to be deployed, and locks the sheath to the delivery assembly 1176 so that they can be simultaneously removed at the end of a closure procedure.

Next, as illustrated in FIG. 11B, the handle can be gently pulled proximally to urge the inner member 1118 against an inner surface 1122 of the vessel wall 1104 by way of a rail 1186 that can extend from a proximal housing portion to the connecting member 1132 engaged with the inner member 1118. An enlarged region of the inner member 1118 can be positioned to span the internal opening of the puncture 1102.

With the inner member 1118 in position, a knob on a proximal housing portion can be rotated to move distal ends 1105, 1113 of a shear tube 1188 and a push tube 1190 in a distal direction. This distal movement can urge an outer member 1120 and a locking member 1134 of the implant assembly from a cavity within a distal end 1117 of a surrounding delivery tube 1192, along the rail 1186 and proximal portions of the connecting member 1132, and through a proximal lumen of a sealing membrane 1126 of the implant assembly 1116 so that the distance between the outer 1120 and inner 1118 members is reduced. Additional rotation of the knob can cause the outer 1120 and locking 1134 members to move further along the connecting member 1132, during which time a distal end of the outer member 1120 can contact an outer surface 1124 of the vessel wall 1104 (by way of the sealing membrane 1126), and the outer member 1120 can be caused to expand against the surrounding sealing membrane 1126, as illustrated in FIG. 11C. Recoil of this outer member expansion can be precluded by the abutting locking member 1134, which can be engaged with the connecting member 1132.

Portions of the connecting member 1132 proximal to the locking member 1134 can now be cut and removed. In an example, a lock associated with the handle can be unlocked to allow proximal and distal housing portions to be rotated relative to one another. Since the proximal end of the shear tube is rotatably secured to the proximal housing portion and the proximal end of the push tube is rotatably secured to the distal housing portion, relative rotation of the housing portions can cause corresponding relative rotation of the distal ends 1105, 1113 of the shear 1188 and push 1190 tubes and their associated keyed passageways. This relative rotation of the keyed passageways can shear the connecting member 1132 so that its proximal portions can be removed.

At this time, the only component remaining attached between the implant assembly 1116 and the delivery assembly 1076 is the sealing membrane 1126. A distal end of the sealing membrane 1126 is attached to the inner member 1118, can extend through portions of the puncture 1102 and surround portions of the outer member 1120, and is attached to the distal end 1117 of the delivery tube 1192 at its proximal end (e.g., using UV adhesive, thermal bonding or solvent bonding). Leveraging perforations (see, e.g., element 1031 in FIG. 10B) in the sealing membrane 1126, the handle can be pulled proximally to tear the sealing membrane 1126 along its perforations 1131 and separate the delivery tube 1192 from the implant assembly 1116. Now separated from the implant assembly 1116, the delivery assembly 1176 and the introducer sheath 1119 can be removed from the patient by further pulling the handle proximally, in a direction away from the patient.

Figure 12:
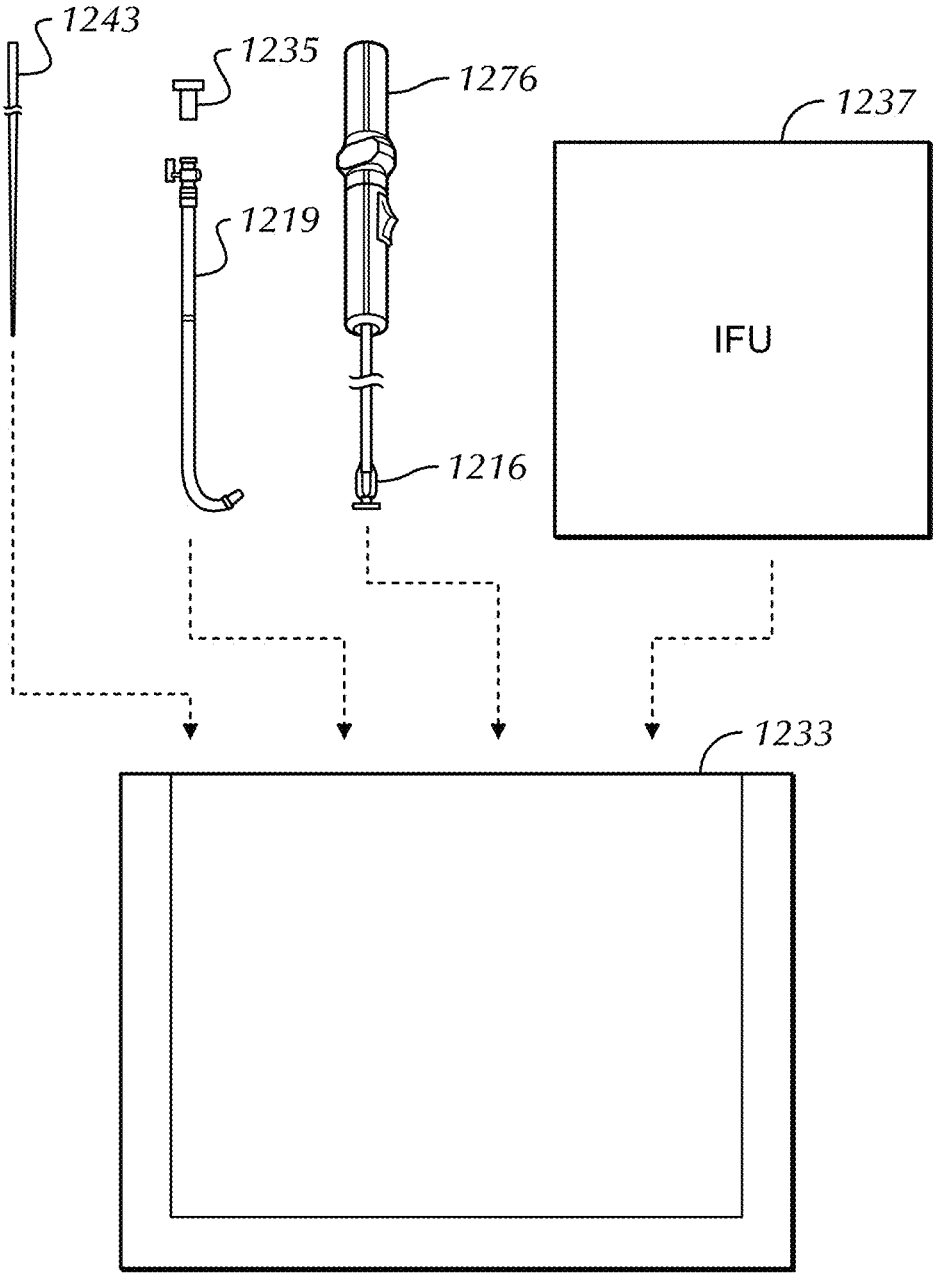
FIG. 12 is a schematic illustration of a kit including an implant assembly, a delivery assembly, an introducer sheath and a valve bypass, a dilator, and instructions for using these components to seal a puncture site or other opening in a blood vessel wall, body cavity or biopsy tract, as constructed in accordance with at least one embodiment of the present teachings.

Closure System Kit:

FIG. 12 is a schematic illustration of a kit 1233 including an implant assembly 1216, a delivery assembly 1276, an introducer sheath 1219 and a valve bypass 1235, a dilator 1243, and instructions 1237 for using these components to seal a puncture or other opening in a blood vessel wall, body cavity or biopsy tract, as constructed in accordance with at least one embodiment. The implant assembly 1216 can come preloaded and attached to distal end portions of the delivery assembly 1276. In this way, a treating clinician, after gaining access to a vessel lumen with the dilator 1243 and introducer sheath 1219, can perform the series of simple steps described and illustrated in FIGS. 11A-11C to seal the puncture site. The dilator 1243 can be relatively long (e.g., about 80 cm or more) and without a proximal hub to facilitate removal of a TAVI sheath or other interventional device, for example.

Closing Notes and Examples

The present closure systems, kits and methods can be used by a treating clinician to seal a puncture or other opening following removal of an introducer sheath or other interventional device, regardless of whether the device's profile is small, medium or large in size. The systems, kits and methods allow for closure of the puncture or opening using a construction that is easy to use, safe, effective and reliable. Implant components of a closure system can dissolve over a period of time while permitting healing of the puncture or opening and the surrounding tissue.

Although the figures and many embodiments relate to use of the present closure systems, kits and methods for sealing of a puncture associated with vascular surgery, one of ordinary skill in the art will appreciate that components disclosed herein are scalable and can be useful for closure of any puncture or other opening in a blood vessel wall, body cavity or biopsy tract of a patient. Further, it is contemplated that the present closure systems, kits and methods can be incorporated into another medical device such that cumulative delivery and deployment steps during a medical procedure are reduced.

The above Detailed Description includes references to the accompanying drawings, which form a part of the Detailed Description. The Detailed Description should be read with reference to the drawings. The drawings show, by way of illustration, specific embodiments in which the present systems, kits and methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a closure system for sealing a hole, which extends between a first tissue surface and a second tissue surface and has a size and an edge, comprises an implant assembly. The implant assembly can include an inner member, an outer member and a sealing membrane. The inner member can be configured to extend at least partially through the hole and have a surface positionable against the first tissue surface. The outer member can expand from a delivery configuration to a sealing configuration and be positioned adjacent the second tissue surface. The sealing configuration can have a size larger than the size of hole. The sealing membrane can have a distal end sealably attached to the inner member, a proximal end including an opening configured to receive the outer member, and a mid-region therebetween. The outer member, when in the sealing configuration, can urge the mid-region of the sealing membrane radially outward such that its outer surface contacts and conforms to the edge of the hole.

In Example 2, the closure system of Example 1 can optionally be configured such that the implant assembly further comprises a connecting member coupled on its distal end to the inner member and extending at an angle relative to the inner member. The connecting member can include one or more surface projections extending along a portion of its length.

In Example 3, the closure system of Example 2 can optionally be configured such that the implant assembly further comprises a locking member including a projection engagement portion, which allows the connecting member to be slid with respect to the locking member in a first direction but precludes the connecting member from sliding with respect to the locking member in a second, opposite direction.

In Example 4, the closure system of any one of Examples 2 or 3 can optionally be configured such that a hinge is incorporated at an intersection of the inner member and the connecting member.

In Example 5, the closure system of any one or any combination of Examples 1-4 can optionally be configured such that the inner member includes an enlarged region between first and second end regions. The first end region can have a length greater than the second end region.

In Example 6, the closure system of Example 5 can optionally be configured such that each of the first and second end regions includes a radiopaque material or a void that is viewable using fluoroscopy or ultrasound.

In Example 7, the closure system of Example 6 can optionally be configured such that the radiopaque material is a water soluble material.

In Example 8, the closure system of any one or any combination of Examples 1-7 can optionally be configured such that the outer member has a proximal end, an intermediate deformation portion, and a distal end. The intermediate deformation portion can include a plurality of struts created by parallel slits or cuts through a wall of the outer member.

In Example 9, the closure system of Example 8 can optionally be configured such that each of the plurality of struts includes a hinge region.

In Example 10, the closure system of any one of Examples 8 or 9 can optionally be configured such that when the outer member is in the delivery configuration, each of the plurality of struts is elongated in a direction substantially perpendicular to the inner member.

In Example 11, the closure system of any one or any combination of Examples 8-10 can optionally be configured such that when the outer member is in the sealing configuration, each of the plurality of struts is contracted in a direction substantially parallel to the inner member.

In Example 12, the closure system of any one or any combination of Examples 8-11 can optionally be configured such that the size of the outer member in the sealing configuration is dependent on an amount of contraction of the plurality of struts.

In Example 13, the closure system of any one or any combination of Examples 1-12 can optionally be configured such that each of the inner member, the outer member, and the sealing membrane includes a bioabsorbable material.

In Example 14, the closure system of Example 13 can optionally be configured such that the bioabsorbable material includes an acidic polymer and an alkaline earth metal.

In Example 15, the closure system of any one or any combination of Examples 1-14 can optionally be configured such that the sealing membrane includes a non-porous material.

In Example 16, the closure system of any one or any combination of Examples 1-15 can optionally be configured such that the sealing membrane includes a micro-porous material having a plurality of micro-pores. Each micro-pore can be sized and shaped to inhibit the flow of blood cells.

In Example 17, the closure system of any one or any combination of Examples 1-16 can optionally be configured such that the sealing membrane includes one or more reinforcing elements.

In Example 18, the closure system of Example 17 can optionally be configured such that the one or more reinforcing elements are arranged parallel to a longitudinal axis of the sealing membrane.

In Example 19, the closure system of Example 17 can optionally be configured such that the one or more reinforcing elements are arranged at an angle relative to a longitudinal axis of the sealing membrane.

In Example 20, the closure system of any one or any combination of Examples 1-19 can optionally be configured such that the sealing membrane includes a non-uniform cross-sectional size between its distal end and its proximal end.

In Example 21, the closure system of any one or any combination of Examples 1-20 can optionally be configured such that the sealing membrane includes one or more perforations near its proximal end.

In Example 22, the closure system of any one or any combination of Examples 1-21 can optionally further comprise a delivery assembly. The delivery assembly can include a handle, a rail, a shear tube, a delivery tube and an actuation member. The handle can have a first housing portion and a second housing portion.

The rail can extend from a first end engaged with the inner member to a second end statically coupled with the second housing portion. The outer member can be supported by the rail between its first and second ends. The shear tube can extend from a first end, which includes a keyed passageway, to a second end engaged with the second housing portion. The delivery tube can concentrically surround portions of the shear tube, be coupled to an end of the sealing membrane on its first end, and be coupled to the first housing portion on its second end. The actuation member can be engaged with the second end of the shear tube to urge the tube in a direction to expand the outer member from its delivery configuration to its sealing configuration.

In Example 23, the closure system of Example 22 can optionally be configured such that the first housing portion is releasably lockable to the second housing portion. In the absence of being locked, the first housing portion can rotate relative to the second housing portion.

In Example 24, the closure system of any one of Examples 22 or 23 can optionally be configured such that the second end of the shear tube is engaged with an axial tract of the second housing portion, thereby confining the shear tube to axial movements relative to the second housing portion.

In Example 25, the closure system of any one or any combination of Examples 22-24 can optionally be configured such that the delivery assembly further comprises a push tube positioned between the shear tube and the delivery tube. The push tube can extend from a first end, which includes a keyed passageway, to a second end engaged with an axial tract of the first housing portion. This axial tract can confine the push tube to axial movements relative to the first housing portion.

In Example 26, a method for sealing a hole that extends between an inner vessel surface and an outer vessel surface can comprise inserting an inner member through the hole and into a lumen of the vessel. The inner member can be pulled against the inner vessel surface and portions of a connecting member and a sealing membrane, which are coupled on their first ends to the inner member, can be arranged to extend to the outside of the vessel on their second ends. An outer member in a delivery configuration can then be inserted through the second end of the sealing membrane such that the sealing membrane at least partially surrounds the outer member. A compressive force can be applied to the outer member in a distal direction to expand the delivery configuration to a sealing configuration. This expansion can urge a mid-region of the sealing membrane radially outward such that its outer surface contacts and conforms to an edge of the hole.

In Example 27, the method of Example 26 can optionally be configured such that applying the compressive force to the outer member includes expanding the outer member to a circumference greater than a perimeter of the hole.

In Example 28, the method of any one of Examples 26 or 27 can optionally further comprise securing a position of the inner member against the inner vessel surface and the expansion of the outer member in the sealing configuration. This securing can include engaging a locking member with a portion of the connecting member.

In Example 29, the method of Example 28 can optionally further comprise changing a circumference of the outer member in the sealing configuration by adjusting a position of the locking member relative to the connecting member.

In Example 30, the method of any one of Examples 28 or 29 can optionally further comprise shearing portions of the connecting member that are proximal of the locking member.

In Example 31, the method of any one or any combination of Examples 26-30 can optionally be configured such that inserting the outer member through the second end of the sealing membrane includes positioning the outer member into a portion of the sealing membrane having a larger cross-sectional size than other portions of the sealing membrane.

In Example 32, the method of any one or any combination of Examples 26-31 can optionally further comprise viewing encapsulated pockets of iodine in the inner member using x-ray.

In Example 33, the method of any one or any combination of Examples 26-32 can optionally further comprise removing excess portions of the sealing membrane along one or more perforations near its second end.

In Example, the system or method of any one or any combination of Examples 1-33 can optionally be configured such that all elements or options recited are available to use or select from.

The scope of the present systems, kits and methods should be determined with reference to the appended claims, along with the full scope of equivalents to which such claims are entitled. In the appended claims, the terms “including” and “in which” are used as the plain-English equivalents of the respective terms “comprising” and “wherein.” Also in the following claims, the terms “including” and “comprising” are open-ended; that is, a system, kit or method that includes features or components in addition to those listed after such a term in a claim are still deemed to fall within the scope of that claim. Moreover, the terms "first," "second" and "third," etc. in the following claims are used merely as labels, and such terms not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method for sealing a hole that extends between an inner vessel surface and an outer vessel surface, comprising:

inserting an inner member including a bioabsorbable material through the hole and into a lumen of a vessel, wherein the inner member is attached to a distal end of a sealing membrane *and a proximal end of the sealing membrane defines an opening and extends outside of the vessel*;

pulling the inner member against the inner vessel surface [, including arranging] *such that* a portion of a connecting member, which is coupled on its distal end to the inner member, [to extend to the] *extends* outside of the vessel[on its proximal end];

[inserting] *positioning* an outer member including a bioabsorbable material in a delivery configuration [over the proximal end of] *slidably along* the connecting member to a position adjacent the outer vessel surface *opposite and spaced from the inner member such that the distance between the outer member and the inner member is adjustable*, wherein the outer member is received within [a] *the opening defined by the* proximal end of the sealing membrane; and applying a compressive force to the outer member, including expanding the outer member from the delivery configuration to a sealing configuration *within the sealing membrane* such that [its outer surface contacts and conforms to an edge of the hole and] the expanded outer member urges a mid-region of the sealing [member] *membrane* radially outward *and enables an outer surface of the sealing membrane to contact and conform to an edge of the hole*.

2. The method of claim 1, wherein inserting the inner member through the hole and into the lumen of the vessel includes positioning an enlarged region of the inner member adjacent to the hole.

[3. The method of claim 1, wherein pulling the inner member against the inner vessel surface includes conforming the inner member to a shape of the inner vessel surface.]

[4. The method of claim 1, wherein pulling the inner member against the inner vessel surface includes activating a hinge at an intersection of the inner member and the connecting member.]

[5. The method of claim 4, wherein activating the hinge includes allowing the connecting member to bend or reorientate with respect to the inner member.]

6. The method of claim 1, wherein pulling the inner member against the inner vessel surface includes maintaining tension on the proximal end of the connecting member.

[7. The method of claim 1, wherein inserting the outer member over the connecting member to the position adjacent the outside of the vessel includes advancing the outer member along the connecting member until it contacts the outer vessel surface.]

8. The method of claim 1, wherein [inserting] *positioning* the outer member [over] *including the bioabsorbable material in the delivery configuration slidably along* the connecting member to the position adjacent the outer vessel surface includes advancing the outer member along the connecting member until it contacts a stop member placed on the connecting member.

9. The method of claim 1, wherein [inserting] *positioning* the outer member [over] *including the bioabsorbable material in the delivery configuration slidably along* the connecting member includes inserting first and second outer members over the connecting member in a stacking arrangement.

[10. The method of claim 9, wherein expanding the outer member from the delivery configuration to the sealing configuration includes expanding the first and second outer members from the delivery configuration to the sealing configuration.]

11. The method of claim 1, wherein expanding the outer member from the delivery configuration to the sealing configuration includes expanding the outer member to a circumference greater than a perimeter of the hole.

12. The method of claim 1, wherein expanding the outer member from the delivery configuration to the sealing configuration includes causing the outer member to assume a longitudinally-compressed and transversely-expanded configuration.

[13. The method of claim 1, wherein expanding the outer member from the delivery configuration to the sealing configuration includes causing a plurality of struts, defined by parallel slits through a wall of the outer member, to move from an orientation substantially perpendicular to the inner member toward an orientation substantially parallel to the inner member.]

[14. The method of claim 1, further comprising securing a position of the inner member against the inner vessel surface and the expansion of the outer member in the sealing configuration, including engaging a locking member with a portion of the connecting member.]

[15. The method of claim 14, wherein the locking member includes an engagement portion configured to allow the connecting member to be slid with respect to the locking member in a first direction, but precluding the connecting member from sliding with respect to the locking member in a second, opposite direction.]

[16. The method of claim 14, further comprising changing a circumference of the outer member in the sealing configuration by adjusting a position of the locking member relative to the connecting member.]

[17. The method of claim 14, further comprising shearing portions of the connecting member proximal of the locking member and removing the portions from an area near the vessel.]

18. The method of claim 1, further comprising viewing an encapsulated pocket of radiopaque material in [each longitudinal] *an* end of the inner member using fluoroscopy.

19. The method of claim 1, further comprising viewing an encapsulated pocket of a water soluble, radiopaque material in the inner member using fluoroscopy.

20. The method of claim 1, further comprising viewing an encapsulated pocket of iodine in the inner member using fluoroscopy.

* * * * *